United States Patent

Kalfa et al.

[11] Patent Number: 5,795,994
[45] Date of Patent: Aug. 18, 1998

[54] PROCESS AND APPARATUS FOR MEASURING CONDENSED MOISTURE AND APPLICATIONS THEREOF

[75] Inventors: Horst Kalfa, Idstein; Knut Schroeder, Frankfurt am Main, both of Germany

[73] Assignee: Metallgesellschaft Aktienegesellschaft, Frankfurt Am Main, Germany

[21] Appl. No.: 755,959

[22] Filed: Nov. 25, 1996

[30] Foreign Application Priority Data

Nov. 24, 1995 [DE] Germany .............. 195 43 770.5

[51] Int. Cl.$^6$ .............. G01N 27/02; G01W 01/11; C23F 13/00
[52] U.S. Cl. .............. 73/29.01; 73/335.04; 73/335.05; 324/439; 324/694; 324/77.1; 204/147; 204/153.1
[58] Field of Search .............. 73/29.01, 335.04, 73/335.05; 324/439, 77.1, 694; 204/153.1, 147

[56] References Cited

U.S. PATENT DOCUMENTS

| | | | |
|---|---|---|---|
| 3,857,284 | 12/1974 | Carron et al. | 73/336.5 |
| 4,011,538 | 3/1977 | Froemel | 338/35 |
| 4,052,667 | 10/1977 | Schwartz | 324/65 P |
| 4,227,411 | 10/1980 | Abramovich | 73/336.5 |
| 4,266,195 | 5/1981 | Keefner et al. | 324/439 |
| 4,795,539 | 1/1989 | Bianchi et al. | 204/147 |
| 4,933,669 | 6/1990 | Lyons | 340/632 |
| 5,097,212 | 3/1992 | Carlon et al. | 324/464 |
| 5,137,991 | 8/1992 | Epstein et al. | 525/540 |
| 5,164,675 | 11/1992 | Howe et al. | 324/690 |
| 5,343,735 | 9/1994 | Succi et al. | 73/29.01 |

Primary Examiner—Hezron E. Williams
Assistant Examiner—J. David Wiggins
Attorney, Agent, or Firm—Michael J. Striker

[57] ABSTRACT

Condensed moisture in devices and/or pipe conduits for anti-corrosion applications in chemical engineering is measured at least one point in the devices and/or pipe conduits by measuring an electrochemical potential difference across two different elements, such as iron and copper, which are arranged one beside the other spaced from 0.001 to 1 mm from each other by an electrically insulating material so as to be electrically insulated from each other. An apparatus for making these measurements is also described.

8 Claims, 2 Drawing Sheets

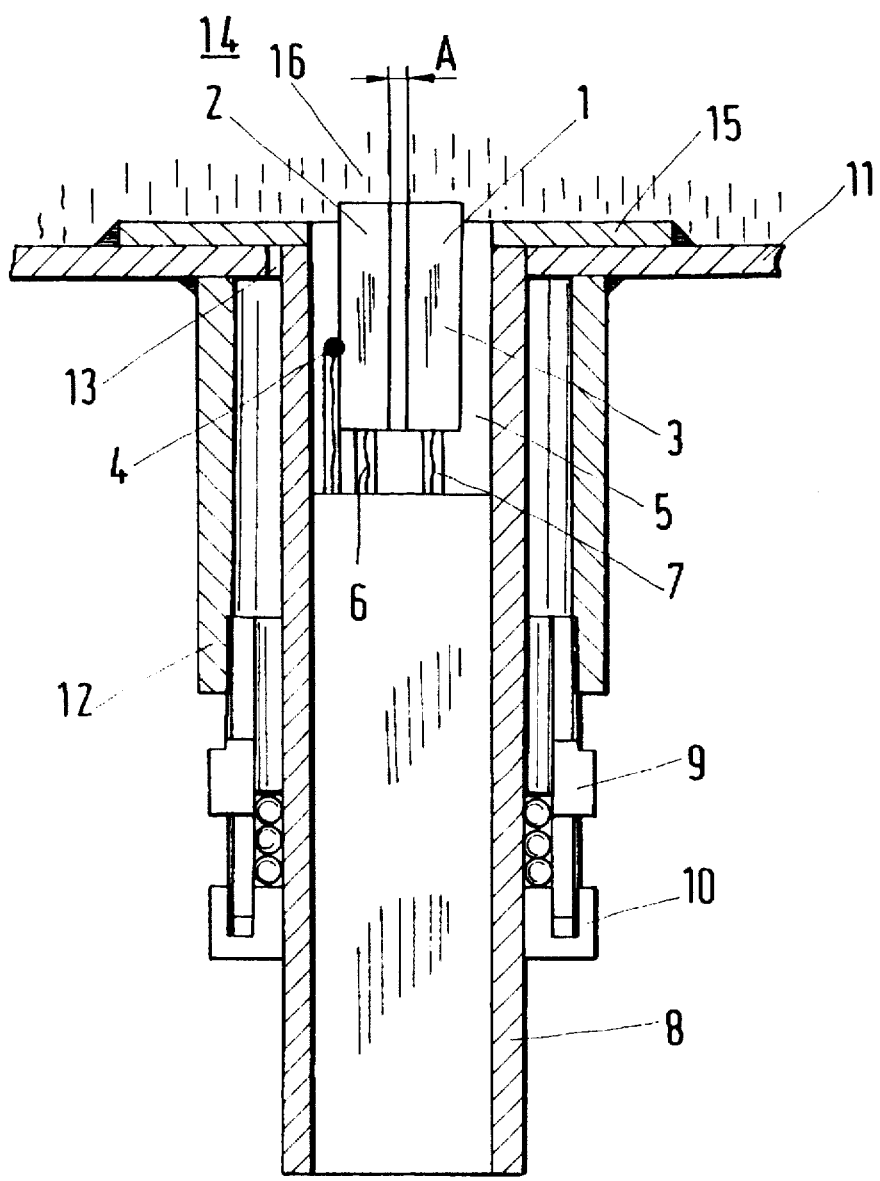

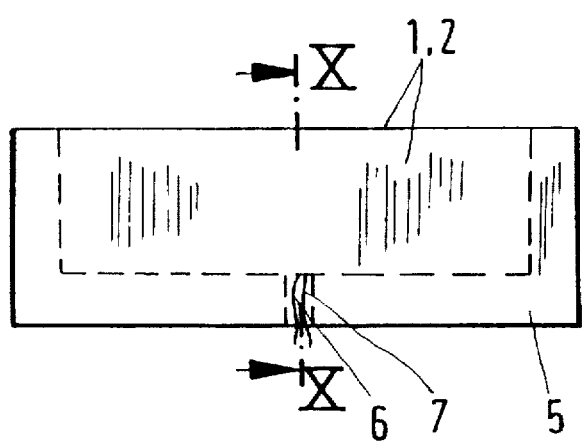
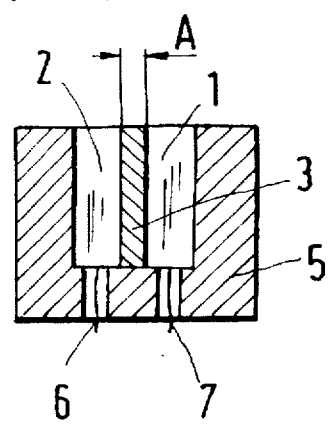
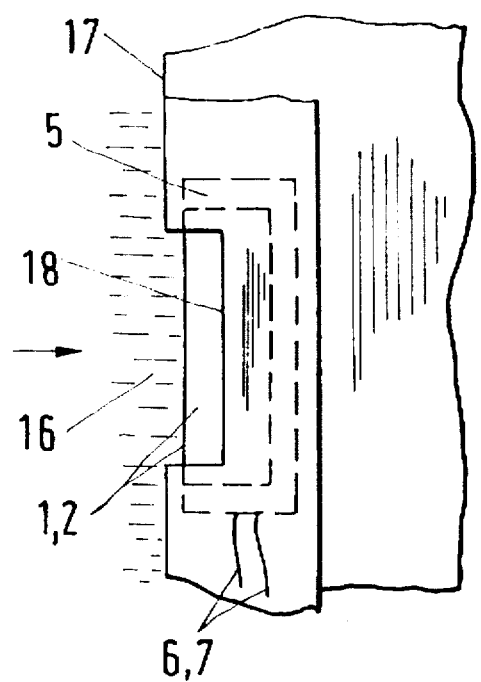

PROCESS AND APPARATUS FOR MEASURING CONDENSED MOISTURE AND APPLICATIONS THEREOF

BACKGROUND OF THE INVENTION

This invention relates to a process and apparatus for measuring condensed moisture, especially in devices and/or pipe conduits of a chemical plant and to various applications utilizing the process and apparatus.

The material used for parts and components in technical plants often is carbon steel, whose surface is attacked by corrosion upon contact with a phase that contains condensed moisture. As used herein, the term "phase" is meant to designate all media that may contain moisture. These include for instance gases, vapors, steams, dusts or powdery substances. The water contained in the phase or an aqueous solution regardless of the physical state is in this connection referred to as "moisture", and its relative mass is referred to as "moisture content". What is meant by the term "corrosion" is the detrimental alteration of the material, which proceeds from the surface and is caused by an unintentional chemical or electrochemical attack. As a protection against corrosion, the carbon steel may be separated mechanically from a moisture-containing phase by means of coatings, protective layers or sheetings, or corrosion-resistant materials may be used. However, such measures involve an increased effort and higher costs, and are mostly unacceptable from an economical point of view. Rather, attempts are being made to design and operate technical plants such that a condensation of the moisture is avoided by a sufficient thermal distance from its dew point. As used herein, the term "dew point" designates the temperature at which the moisture liquefies at the existing partial pressure, i.e. the steam pressure corresponding to the moisture content.

Corrosion cannot always be prevented in plants or pipe conduits for chemical engineering. As used herein, the term "plants for chemical engineering" is meant to designate all plants used in chemical technology and related fields, including for instance plants of mechanical process technology, where corrosion problems, for instance in carbon steel, can in particular be due to changing operating conditions and alterations of the phases that come in contact with carbon steel. These include, for instance, plants in the steel industry, construction materials industry, chemical industry, ferrous and non-ferrous metals and glassworks industry, cellulose industry as well as fuel and energy technology, when changing operating conditions and alterations of phases during-the operation can often not be determined precisely enough. In plants for cleaning dust-laden exhaust gases, for example, a phase containing condensed moisture may be produced due to the hygroscopic behavior of the dusts in the exhaust gases and due to the adsorption or absorption of moisture, where the occurrence thereof depends on a plurality of parameters and is hardly predictable. It is therefore necessary to measure the occurrence of condensed moisture in these phases, so as to reduce the moisture content and avoid a further condensation by means of a corresponding control of the operation of the technical plants. There is, however, the problem that these phases may have a very high dust loading of any composition. In particular, dust deposits may be found on the walls of technical plants, which are particularly susceptible to corrosion. The additional problem is that certain technical plants require a direct measurement of condensed moisture in a fixed bed.

For measuring the moisture in gases, hygrometers in the form of hair hygrometers, conductivity hygrometers, electrolytic hygrometers, diffusion hygrometers and psychrometers are used. The hygrometers have, the disadvantage that they are very susceptible to contamination, or that a measurement is not possible as the substance to be analyzed undergoes a chemical reaction with the gas. In the case of liquids and solids the moisture can be measured by drying or by means of physical measuring methods in the form of a conductivity measurement, thermogravimetric measurement, infra-red absorption and through a determination by means of high-speed neutrons. In addition, chemical processes are commonly used. These processes are relatively complex and are mostly used for analytical purposes only. For measuring the moisture content in plants for chemical engineering, none of the above-stated measuring methods is suited.

SUMMARY OF THE INVENTION

It is an object of the present invention to provide a process for measuring condensed moisture in devices and pipe conduits for chemical engineering which is easily accomplished in technical terms and readily integrated into an existing system for operating and controlling a plant.

The process according to the invention comprises the step of measuring at least one difference of electrochemical potentials between at least two elements arranged one beside the other and electrically insulated from each other at least one point in the devices and/or pipe conduits by means for measuring the at least one difference in electrochemical potentials. Each of the at least two elements are made of materials having different electrochemical potentials.

The measurement of moisture is based on the principle of electrolytic polarization due to unequal polarization voltages, which occurs in the presence of an electrolyte between elements having a different electrochemical potential. When the phase between the elements contains condensed moisture, it acts as an electrolyte, and there is produced an electric voltage between the elements having a different electrochemical potential. The magnitude of this electric voltage depends on the difference in the electrochemical potentials, the composition of the phase, the temperature and the ohmic resistance between the elements. The materials to be used for these elements include for instance metals, metal alloys, and ceramic materials such as silicon carbide and graphite. The external shape of the elements must therefore be adapted to the respective use. For instance, the elements may have a rectangular or semicircular cross-section. The elements are arranged one beside the other electrically insulated from each other, which may occur by mounting the elements on a common substrate made of an electrically insulating material. The difference of the electrochemical potentials of the elements can for instance be measured by means of a high-impedance voltmeter. The high-impedance voltmeter should possibly have an internal resistance larger than $10^{12}$ Ohm. The advantage is that the measurement signal can be evaluated directly and can be incorporated into the system for operating the technical plant for monitoring and/or control purposes. The electric voltage measured may serve as "online signal", which means that the operation of the technical plant is correspondingly adjusted when the signal changes. The interference with the operation or the control depends on the temperature and moisture gradient in the technical plant. In the presence of condensed moisture, the temperature in the plant or pipe conduit will be increased, for instance, and/or the introduction of moisture will be reduced, so that a sufficient thermal distance from the dew point of the moisture is ensured. This may, for instance, be effected by regulating a heating device and/or a cooling device. In the case of a reactor where moisture is injected, the temperature can be influenced by a corresponding control of the amount of moisture injected. Likewise, the use of materials to be processed in the plant, which have a different moisture content, may help to regulate the moisture content. If the phase between the elements does not contain condensed moisture, i.e. its content of condensed moisture is smaller than about 1%, there will be no electric voltage between the different elements and no interference with the operation of the technical plant. In this way, corrosions of non-corrosion-resistant materials in technical plants and pipe conduits, in particular carbon steel, at temperatures below about 200° C. due to condensed moisture can relatively safely be avoided. By means of the process in accordance with the invention a quantitative determination of the content of condensed moisture can also be performed. For this purpose, comparative graphs are plotted, which show the course of the signal resulting from the measurement of the difference of the electrochemical potentials at different contents of condensed moisture and at different temperatures. By comparing the actual data with these comparative graphs the actual content of condensed moisture is thus determined, and the technical plant is controlled such that the desired content of condensed residual moisture is achieved.

In accordance with a further aspect of the invention the difference of the electrochemical potentials is measured between at least two elements which consist of different metals or metal alloys. The-materials for these elements are selected such that, in addition to a sufficient difference in their electrochemical potentials, they also have a relatively high chemical resistance to the surrounding medium, in order to achieve a sufficient service life of the sensor.

In accordance with a further aspect of the invention the difference of the electrochemical potentials is measured between two different elements, iron and copper or titanium and zirconium. The materials iron and copper are relatively inexpensive and easy to work and exhibit a sufficiently high resistance to corrosion in many applications. For highly corroding phases, for instance phases with condensed hydrochloric acid, the materials titanium and zirconium are preferably used due to their relatively high corrosion resistance, so as to ensure a sufficiently long service life of the elements.

In accordance with a further aspect of the invention the temperature of at least one element is measured. The measurement of the temperature is advantageous since the magnitude of the electric voltage between the elements having different electrochemical potentials also depends, on the temperature. A temperature measurement is advantageous in particular when by means of the process in accordance with the invention a quantitative determination of the content of condensed moisture should be effected.

In accordance with a further aspect of the invention the difference of the electrochemical potentials of the elements is supplied via a shielded cable to the measuring device, flashover voltages are first of all filtered, and then the difference of the electrochemical potentials is converted for adaptation to the control circuit of the technical plant. This procedure can advantageously be used in particular for measuring condensed moisture in high-voltage plants, for instance in electrostatic precipitators. As a filtering device for the flashover voltages, for instance a high voltage surge protector with relatively short response times can be used, which is used for the protection of persons and instruments. The resulting voltage signals are converted into currents of 4 to 20 mA, which can be introduced into the control circuit of the technical plant.

In accordance with a further aspect of the invention the inventive process is carried out by means of an apparatus comprising at least two elements which are separated from each other by an electrically insulating material. The distance between the elements is from 0.001 to 1 mm, the elements consist of materials having a different electrochemical potential and are arranged one beside the other and electrically insulated from each other. The electrically insulating material can, for instance, be an electrically insulating plastic material. For use at elevated temperatures polytetrafluoroethylene (PTFE) is, for instance, very well suited. In the technical plant or pipe conduit the elements are for instance arranged such that they are seated in the wall of such plant or conduit, or that the tips of the elements protrude into the interior through the wall or terminate flush with the surface of this wall.

In accordance with a further aspect of the invention the apparatus comprises at least two elements which consist of materials having a different electrochemical potential and are mounted on a substrate. The substrate is arranged inside a first cylindrical pipe section. The first cylindrical pipe section is connected with a second cylindrical pipe section by a frictional and positive connection and the second cylindrical pipe section is mounted on a wall of a technical plant so that the tips of the two elements extend through a bore provided in this wall into the interior of the technical plant or terminate flush with the surface of this wall. The frictional and positive connection may for instance be effected by means of a screw connection, in which the first cylindrical pipe section is provided with a male thread and is screwed into a second cylindrical pipe section provided with an appropriate female thread. The advantage of this apparatus for measuring condensed moisture is that it can be installed in the technical plant even subsequently, i.e. after the set-up of the technical plant. Even a replacement of this apparatus is very easily possible. One or several of these apparatuses are installed in the plant at those points which run the greatest risk of being corroded by condensed moisture.

In accordance with a further aspect of the invention the process and the apparatus for monitoring and/or controlling moisture is used in a plant for drying. The process is for instance very well suited for plants for drying coal, sewage, sludge, and waste or special waste. In such plants it is particularly advantageous that the measurement of the moisture can also be effected directly in the fixed bed of the drying device. Since the residual moisture content can be determined quantitatively, it is possible to control the drying device by means of the inventive process and thus adjust the desired residual moisture content of the product.

In accordance with a further aspect of the invention the process and the apparatus are used for monitoring and/or controlling moisture in a plant for cleaning exhaust gases. The plant can for instance be an electrostatic precipitator or a bag filter. The particular advantage of the inventive process consists in that the moisture of the raw gas can even be measured at any level of dust loading and at a variable composition.

In accordance with a further aspect of the invention the process and the apparatus are used for monitoring and/or controlling moisture in a dry desulfurization plant with a circulating fluidized bed. In this connection it is advantageous that the moisture content can be measured directly in the fluidized bed.

BRIEF DESCRIPTION OF THE DRAWINGS

The objects, features and advantages of the invention will now be illustrated in more detail with the aid of the following description of the preferred embodiments, with reference to the accompanying figures in which:

FIG. 1 is a cross-sectional view through a device for measuring moisture in an apparatus mounted on a wall of the apparatus; and FIGS. 2a, 2b and 2c are views showing a device for measuring moisture in an electrostatic precipitator.

DESCRIPTION OF THE PREFERRED EMBODIMENTS

Embodiment Example 1

The method of measurement of condensed moisture on the wall of an apparatus is now explained by way of example.

The device for carrying out such measurement is represented in FIG. 1 and comprises two elements 1, 2 which are separated a distance A of 0.2 to 0.5 mm from each other by an electrically non-conductive plastic material 3, for instance polytetrafluoroethylene (PTFE). The element 1 consists of iron, and the element 2 is made of copper. A measuring device 4 for determining the temperature is provided in addition on the element 2. The elements 1, 2 are mounted on a substrate 5 provided with bores for the electrical connection lines 6, 7 put on the elements 1, 2, through which the measurement signal is conducted for further signal processing. The substrate 5 is disposed inside a first cylindrical pipe section 8, which is connected with a second cylindrical pipe section 12 mounted on the apparatus wall 11 by means of a thread and stuffing boxes 9, 10. The second cylindrical pipe section 12 is mounted axially on a bore 13 in the apparatus wall 11, so that the tips of the elements 1, 2 protrude into the interior 14 of the apparatus by a few millimeters. For sealing the interior 14 of the apparatus, a sealing diaphragm 15 is additionally mounted on the inside of the apparatus wall 11.

The condensed moisture is determined by measuring the difference of the electrochemical potentials of the two elements 1, 2. When the phase 16 on the apparatus wall 11 contains condensed moisture, an electric voltage is produced between the elements 1 and 2. The voltage signal is converted to an ma-signal of 4 to 20 mA. The mA signal will be directly included in the control system of the technical plant. For example, for reducing the moisture at the apparatus wall the temperature in the apparatus, for example, will be increased.

Embodiment Example 2

The method of measurement of condensed moisture in an electrostatic precipitator will now be described by way of an example.

The device used for this measurement is represented in FIGS. 2a, 2b and 2c. FIG. 2a and FIG. 2b illustrate the device in a longitudinal section and in cross-section. In FIG. 2c the installation of the device in the electrostatic precipitator is represented. The device consists of two elements 1, 2 which are separated a distance A of 0.2 to 0.5 mm from each other by means of an electrically non-conductive plastic material 3, for instance polytetrafluoroethylene (PTFE). The element 1 consists of iron, and the element 2 is made of copper. The elements 1, 2 are mounted on a substrate 5 and provided with electrical connection lines 6, 7 by means of which the measurement signal is supplied to further signal processing devices. The substrate 5 is fixed in the electrostatic precipitator to a precipitation electrode 17, which is provided with a recess 18, by means of a clamping connection by bending the sheet metal of the electrodes.

For measuring condensed moisture the difference of the electrochemical potentials of the two elements 1, 2 mounted on the electrode 17 is measured. The gas to be cleaned flows past the electrode in the direction of arrow. When the phase 16 contains condensed moisture, an electric voltage is produced between the elements 1 and 2. The voltage signal is supplied via the electrical connection lines 6, 7 for further signal processing and is then included in the control system of the technical plant. To reduce the moisture, the temperature of the gas to be cleaned is increased.

While the invention has been illustrated and described as embodied in a process and apparatus for measuring condensed moisture, it is not intended to be limited to the details shown, since various modifications and changes maybe made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

1. A process for monitoring and/or controlling moisture in devices and/or pipe conduits which are part of a dry desulfurization plant with a circulating fluidized bed, said process comprising the step of measuring at least one difference of electrochemical potentials between at least two elements (1, 2) arranged one beside the other and electrically insulated from each other at at least one point in the devices and/or pipe conduits by means for measuring said at least one difference of electrochemical potentials, each of said at least two elements consisting of materials having different electrochemical potentials.

2. A process for monitoring and/or controlling moisture in devices and/or pipe conduits which are part of a dry desulfurization plant with a circulating fluidized bed, said process for monitoring and/or controlling moisture comprising operating an apparatus comprising at least two elements (1, 2) made of different materials having different electrochemical potentials and arranged one beside the other and separated by a distance (A) of from 0.001 to 1 mm from each other by an electrically insulating material (3) so as to be electrically insulated from each other;

means for measuring at least one electrochemical potential difference between said at least two elements; and a second cylindrical pipe section (12) mounted on a wall (11) of a technical plant over a bore (13) provided in said wall, a first cylindrical pipe section (8) connected to the second cylindrical pipe section (12) by a frictional and positive connecting means, and a substrate (5) mounted inside the first cylindrical pipe section (8), and wherein said at least two elements (1, 2) have tips and are mounted on the substrate (5) so that said tips extend through said bore provided in said wall (11) into an interior of the technical plant or said tips extend up to said bore provided in said wall and terminate flush with said wall.

3. The process as defined in claim 1, wherein each of the at least two elements consists of a different member selected from the group consisting of metals and metal alloys.

4. The process as defined in claim 3, wherein said at least two elements consist of iron and copper.

5. The process as defined in claim 3, wherein said at least two elements consist of titanium and zirconium.

6. The process as defined in claim 1, further comprising measuring a temperature of at least one of said at least two elements.

7. The process as defined in claim 1, further comprising supplying said at least one difference of electrochemical potentials via shielded cable to said means, for measuring to obtain a measured difference after filtering flashover voltages to obtain a measured difference and then converting said measured difference for adaptation toga control circuit of a technical plant.

8. An apparatus for measuring condensed moisture in devices and/or pipe conduits for corrosion-inhibiting applications in chemical engineering, said apparatus including at least two elements (1, 2) made of different materials having different electrochemical potentials and arranged one beside the other and separated by a distance (A) of from 0.001 to 1 mm from each other by an electrically insulating material (3) so as to be electrically insulated from each other;

means for measuring at least one electrochemical potential difference between said at least two elements;

a second cylindrical pipe section (12) mounted on a wall (11) of a technical plant over a bore (13) provided in said wall, a first cylindrical pipe section (8) connected to the second cylindrical pipe section (12) by a frictional and positive connecting means, and a substrate (5) mounted inside the first cylindrical pipe section (8), and wherein said at least two elements (1, 2) have tips and are mounted on the substrate (5) so that said tips extend through said bore provided in said wall (11) into an interior of the technical plant or said tips extend up to said bore provided in said wall and terminate flush with said wall.

* * * * *